(12) United States Patent
Kfir

(10) Patent No.: US 9,861,373 B2
(45) Date of Patent: Jan. 9, 2018

(54) ASSEMBLY FOR MANIPULATING BONES

(71) Applicant: Efraim Kfir, Petach-Tikva (IL)

(72) Inventor: Efraim Kfir, Petach-Tikva (IL)

( * ) Notice: Subject to any disclaimer, the term of this patent is extended or adjusted under 35 U.S.C. 154(b) by 429 days.

(21) Appl. No.: 14/667,672

(22) Filed: Mar. 24, 2015

(65) Prior Publication Data

US 2015/0289886 A1  Oct. 15, 2015

Related U.S. Application Data

(60) Provisional application No. 61/979,169, filed on Apr. 14, 2014, provisional application No. 61/980,670, filed on Apr. 17, 2014.

(51) Int. Cl.
*A61B 17/16* (2006.01)

(52) U.S. Cl.
CPC ...... *A61B 17/1604* (2013.01); *A61B 17/1626* (2013.01); *A61B 17/1628* (2013.01)

(58) Field of Classification Search
CPC ............ A61B 17/1604; A61B 17/1626; A61B 17/1628
USPC ............ 606/84; 433/121, 123, 132; 173/202
See application file for complete search history.

(56) References Cited

U.S. PATENT DOCUMENTS

| | | | | |
|---|---|---|---|---|
| 1,483,085 A * | 2/1924 | Heidbrink | .......... | A61B 17/1604 606/84 |
| 1,837,067 A * | 12/1931 | Reiter | ................ | A61B 17/1604 433/151 |
| 2,098,495 A * | 11/1937 | Greenberg | ............... | A61C 1/07 173/115 |
| 2,124,024 A * | 7/1938 | Alkin | ................. | A61B 17/1604 29/557 |
| 2,588,006 A * | 3/1952 | Hufnagel | ................. | A61C 3/08 173/117 |
| 4,298,074 A * | 11/1981 | Mattchen | ........... | A61B 17/1624 173/129 |
| 7,569,057 B2 * | 8/2009 | Liu | ...................... | A61B 17/025 606/171 |
| 2012/0172939 A1 * | 7/2012 | Pedicini | ............. | A61B 17/1604 606/86 R |

\* cited by examiner

*Primary Examiner* — Pedro Philogene
*Assistant Examiner* — David C Comstock
(74) *Attorney, Agent, or Firm* — Smith Tempel Blaha LLC; Gregory Scott Smith

(57) ABSTRACT

An elongated-shaped chisel used for bone manipulation during oral surgery. The chisel has a body with a top edge at one end that is configured to interface with a hammer, and a pointed edge at the other end to interface with the bone. An elongated-shaped sleeve surrounds the body of the chisel. A movement-control mechanism that is configured to control the movement of the chisel in relationship to the sleeve, wherein the movement-control mechanism comprises a first section that is associated with the elongated-shaped chisel and a second section that is associated with the elongated-shaped sleeve.

26 Claims, 4 Drawing Sheets

ASSEMBLY FOR MANIPULATING BONES

FIELD OF THE DISCLOSURE

The present disclosure relates to an assembly for practicing bone manipulation. Wherein the bone manipulation can comprise breaking, chiseling, stretching a bone for bone grafting or bone construction or bone fragments movement or creating a cavity, etc. and more particularly the present disclosure is related to the field of dental surgery.

BACKGROUND

Chiseling is common operation in medical surgery. Doctors use different chisels for manipulating bones in some dental surgeries especially in bone augmentation, bone splitting or close maxillary sinus floor augmentation (breaking the sinus floor), plastic surgery, orthopedic surgeries, bone condensing, otonasolaryngology, etc. In common surgery, a doctor (Dr.) can hold an appropriate chisel in one hand, placing the chisel on the bone at a wanted place and in a certain orientation and hammering on top of the chisel with a hammer. The force and the direction of the impact depend on the practioner's (the doctor's) skills.

The entire process of common chiseling is not controllable and predictable. The orientation of the chisel and the intensity of the strike cannot be configured hence, the consequential direction and impact of the force are poorly controlled by the operator. Advanced planning and configuration of chiseling according to the condition of the bone and the desired result, is not feasible. The orientation and the force depend on the skill and the experience of the doctors. Consequently, the direction and the amplitude of the movement of the chisel are not controlled. The unpredictable or uncontrolled movements lead to medical complications. Surgeries that terminate with broken bone, accidental rupture of the sinus membrane, brain concussion, vertigo, etc.

SUMMARY

The deficiencies of a common chisel, which were described above are not intended to limit the scope of the inventive concepts of the present disclosure in any manner. The deficiencies are presented for illustration only. The disclosure describes a plurality embodiments of novel medical chisels/osteotomes and to method of using the novel medical chisel in medical surgeries such as but not limited to dental surgeries.

An example embodiment, among other benefits, provides a configurable chisel. In some embodiment the scope of the movement of the chisel can be configured. In some embodiments the range can be adjusted before the beginning of each surgery. In other embodiments, the range can be a fixed range according to the structure of the chisel. Some embodiment of the novel chisel can use a configurable force for striking on a bone. Along the disclosure and the claims the terms power and force may be used interchangeably. The force of the strike can be configured and adjusted before each surgery or adjusted during the procedure depending on the situation. In alternate embodiment, the force of the strike can be fixed and be defined by the structure of the chisel to a certain force and advancement into the certain tissue (the degree of penetration).

Yet some of the embodiments of the novel chisel can comprise a leading sleeve. The leading sleeve can be a straight one or can have one or more curves. The leading sleeve can be configured to lead the pointed-edge of the chisel to the appropriate location on the bone and in the appropriate orientation. Some embodiments that have a curved-leading-sleeve that transfers the strike to the pointed-edge of the chisel.

In some embodiment, of the disclosed chisel, the strike can be delivered by a releasing stored mechanical energy such as but not limited to mechanical energy that is stored in a loaded spring. The displacement of the spring in order to load it (by pulling or pushing) before releasing it to strike on the chisel can be adjusted to configurable amplitude. In some embodiments, stretching the spring to the preload position can be done manually by one or more levers for example. Releasing of the spring can be done by a mechanical trigger that can be squeezed manually. Alternatively, stretching the spring to the preload position and releasing it can be done by an electrical mechanism or a pneumatic mechanism, etc.

Some embodiments of the disclosed chisel can comprise any combination of the mentioned features. The disclosed chisel delivers a safer and more reliable bone manipulation. In addition, embodiments of the disclosed chisel provide exact extent of the movement of the chisel as well as the impact on the bone to avoid accidental bone fracture or rupture of the sinus membrane and other adverse effects. The result of the surgery with the novel chisel can be preconfigured and yielding the desirable and predictable results while minimizing potential patient harm.

These and other aspects of the disclosure will be apparent in view of the attached figures and detailed description. The foregoing summary is not intended to summarize each potential embodiment or every aspect of the present disclosure, and other features and advantages of the present disclosure will become apparent upon reading the following detailed description of the embodiments with the accompanying drawings and appended claims.

Furthermore, although specific exemplary embodiments are described in detail to illustrate the inventive concepts to a person skilled in the art, such embodiments are susceptible to various modifications and alternative forms. Accordingly, the figures and written description are not intended to limit the scope of the inventive concepts in any manner.

BRIEF DESCRIPTION OF THE DRAWINGS

Exemplary embodiments of the present invention will be understood and appreciated more fully from the following detailed description, taken in conjunction with the drawings in which.

DETAILED DESCRIPTION OF DIFFERENT EMBODIMENTS

Figure 1:
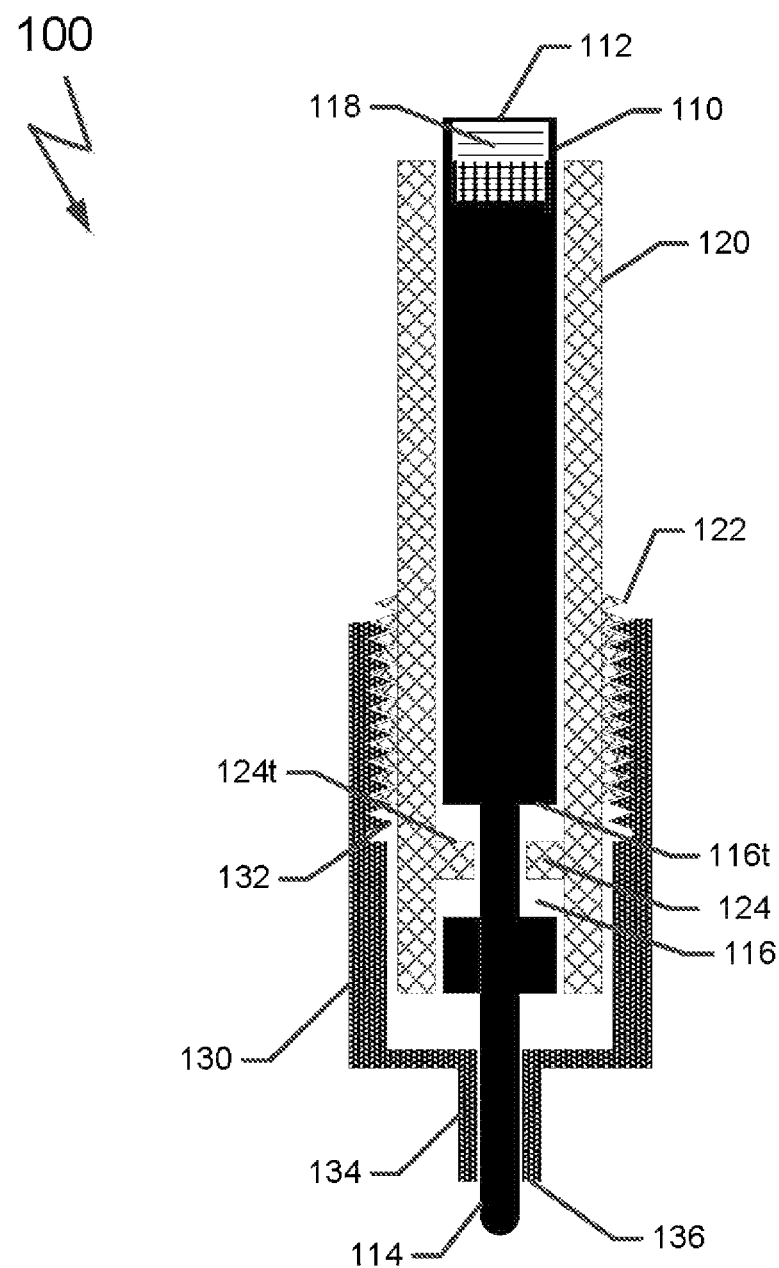
FIG. 1 illustrates a cross-section view with relevant elements of an example embodiment of a configurable chisel in which an external hammer is used (not shown in the figure)

Turning now to the figures in which like numerals represent like elements throughout the several views, different embodiments of the chisel, as well as features, aspects and functions that may be incorporated into one or more such embodiments, are described. For convenience, only some elements of the same group may be labeled with numerals. The purpose of the drawings is to describe different embodiments and not for production. Therefore features shown in the figures are chosen for convenience and clarity of presentation only. It should be noted that the figures are for illustration purposes only and are not drawn to scale. Moreover, the language used in this disclosure has been principally selected for readability and instructional purposes, and may not have been selected to delineate or circumscribe the inventive subject matter, resort to the claims being necessary to determine such inventive subject matter. It should be noted that along the description the directions up, down, left or right are used from the point of view of the reader, while looking on the drawings.

In the following description, for purposes of explanation, numerous specific details are set forth in order to assist in the understanding of the invention. It will be apparent, however, to one skilled in the art that the invention may be practiced without these specific details. In other instances, structures and devices are shown in block diagram form in order to avoid obscuring the invention. References to numbers without subscripts or suffixes are understood to reference all instances of subscripts and suffixes corresponding to the referenced number. Moreover, the language used in this disclosure has been principally selected for readability and instructional purposes, and may not have been selected to delineate or circumscribe the inventive subject matter, resort to the claims being necessary to determine such inventive subject matter.

Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Turning now to the figures in which like numerals represent like elements throughout the several views, different embodiments of the configurable chisel, as well as features, aspects and functions that may be incorporated into one or more such embodiments, are described. For convenience, only some elements of the same group may be labeled with numerals. The purpose of the drawings is to describe different embodiments and not for production. Therefore features shown in the figures are chosen for convenience and clarity of presentation only. It should be noted that the figures are for illustration purposes only and are not drawn to scale. Moreover, the language used in this disclosure has been principally selected for readability and instructional purposes, and may not have been selected to delineate or circumscribe the inventive subject matter, resort to the claims being necessary to determine such inventive subject matter.

FIG. 1 illustrates a cross-section view of relevant elements of an example embodiment of an external-force-configurable chisel (EFCC) 100 in which an external hammer is used. The external hammer is not shown in the figure. An embodiment of the external-force-configurable chisel (EFCC) 100 may be comprised of an elongated-shaped body of the chisel 110, an elongated-shaped protecting sleeve 120 and a leading casing 130. The protecting sleeve 120 may have an outer screw-threaded (OST) 122, and a protrusion 124. The body of the chisel 110 is longer than the protecting sleeve 120. The leading casing 130 can comprise a wide section that surrounds the sleeve and is coupled to the sleeve. The EFCC 100 can be in different sizes and/or shapes in order to comply with the requirement of different treatments.

The leading casing 130 may be comprised of an inner screw-threaded (IST) 132, a penetrating section 134 and a supporting edge 136. The penetrating section can be configured to penetrate into a hole in the bone or a tooth that was prepared by drilling, for example, as a preparation stage to the chiseling. The supporting edge 136 is used for interfacing with the bone around the area, which is planned to be manipulated, in order to reduce the impact of the hammer into less traumatic one. Some embodiments of EFCC 100 may not have the adjustable mechanism of OST 122 and IST 132, instead the sleeve 120 and the leading sleeve may be in a fix position between each other. Other example embodiments of EFCC (not shown) may comprise the body of the chisel 110 and the protecting sleeve 120 without the leading casing 130 and the outer-screw-threaded 122 and IST 132.

Figure 2:
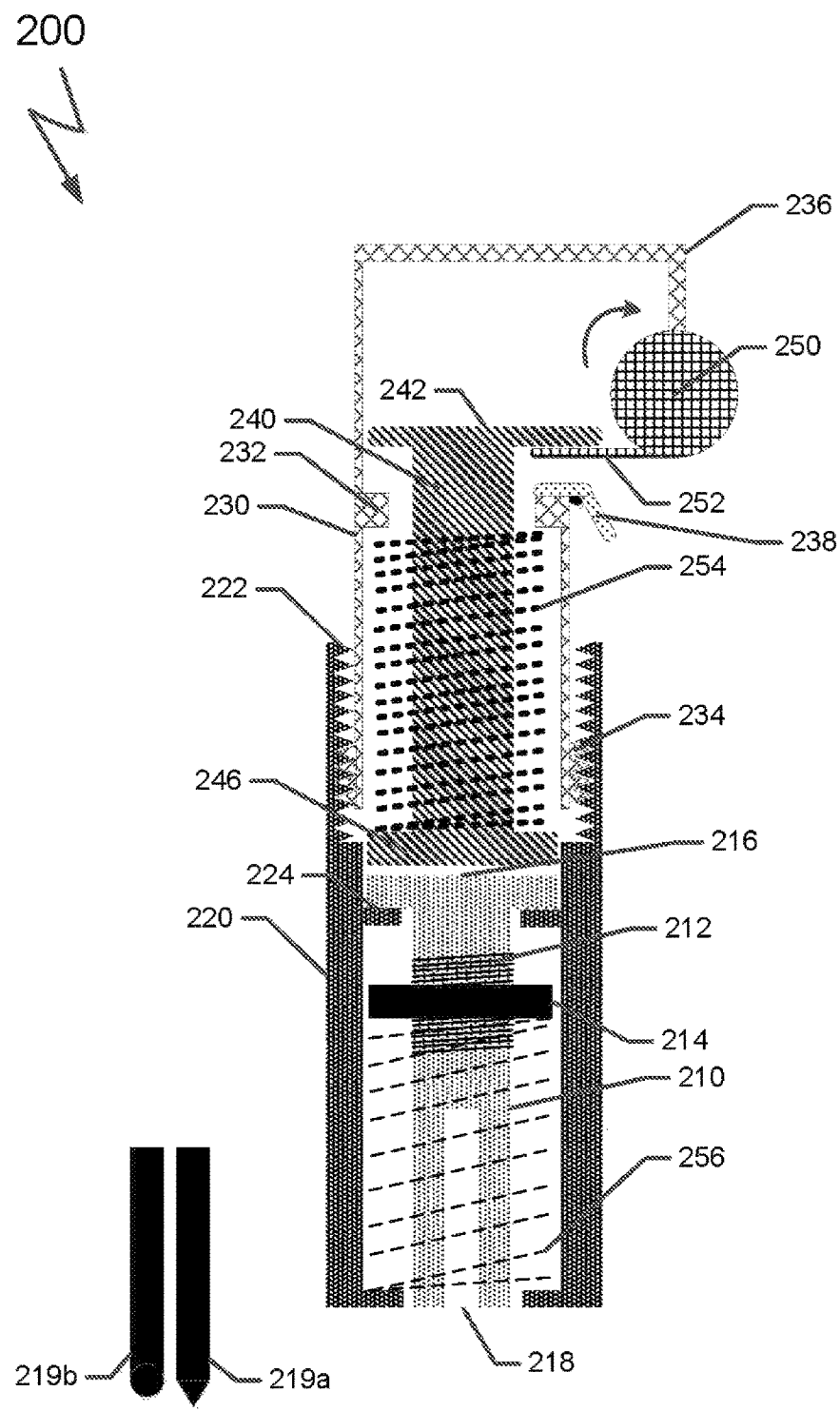
FIG. 2 illustrates a cross-section view with relevant elements of an example embodiment of a configurable chisel in which an internal electronic or pneumatic hammer is used.
Figure 3:
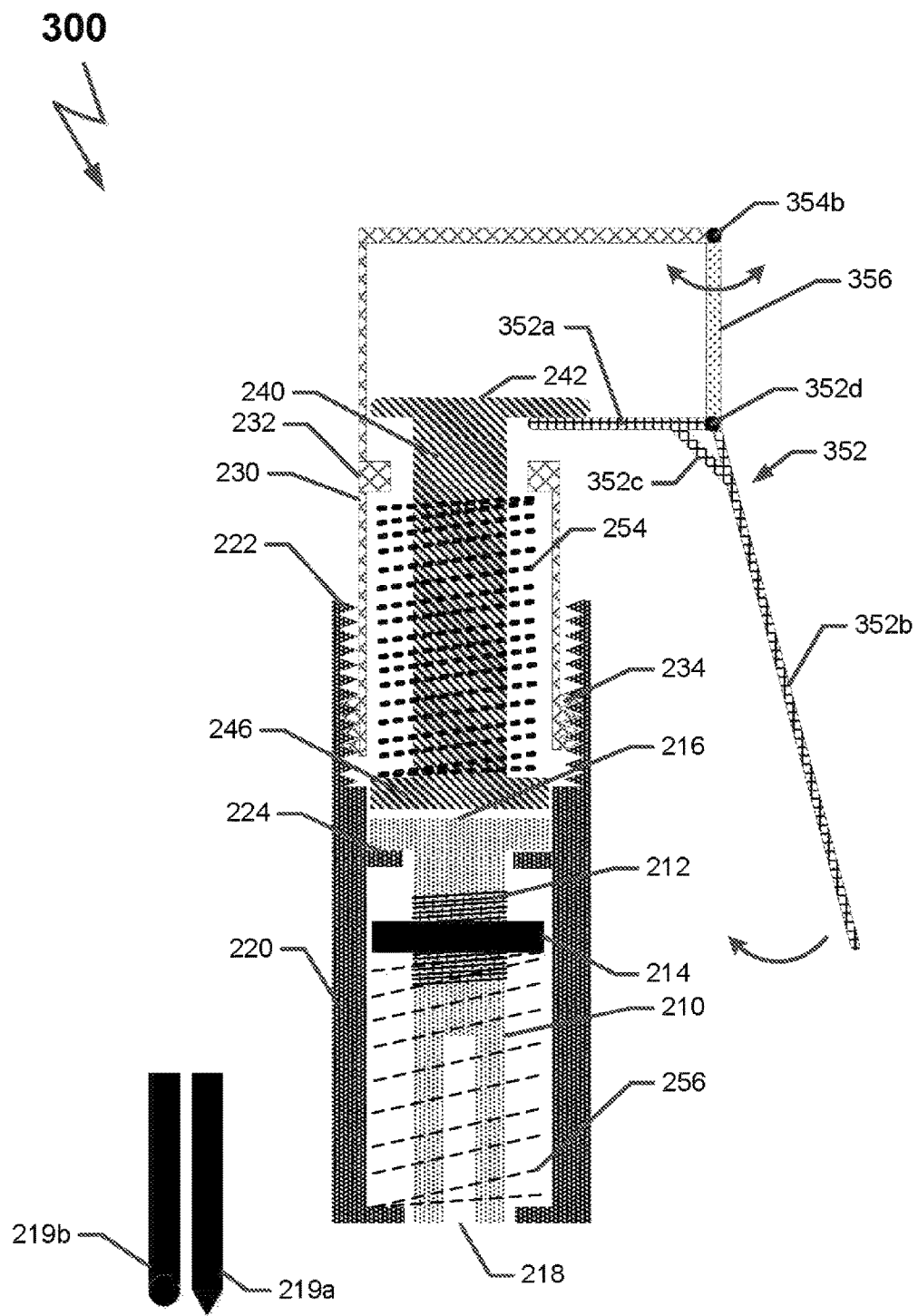
FIG. 3 illustrates a cross-section view with relevant elements of an example embodiment of a configurable chisel in which an internal manual hammer is used.

An example of the body of the chisel 110 may comprise a top edge 112, a pointed-edge 114, a recess 116 and a ruler 118. The maximum depth to which the pointed edge 114 can penetrate in the bone can be defined by the length of the recess 116 minus the length of the protrusion 124. The pointed edge 114 of the chisel can be surrounded by the penetrating section 134 without attaching it. The length of the ruler 118 can be equal to the maximum depth starting from the top edge 112. In this example, the length of the recess 116 is fixed at the manufacturing of EFCC 100. Depending on the maximum required penetration, the appropriate EFCC 100 can be selected by the doctor. The length of recess 116 can be in the range of 0.1-10 mm, for example. Other embodiments of EFCC, which are not shown in the figures, may comprise another adjustable mechanism to define the maximum depth, such as the one that is illustrated in FIGS. 2 or 3, instead of recess 116. The scope of the movement of the pointed edge 114 while hammering on the top edge 112 can be limited by the top edge 124t of the protrusion 124 and the top edge 116t of the recess 116. The recess 116 and the protrusion 124 are two sections of a movement-control mechanism. In other embodiments of movement-control mechanism, the protrusion can be associated with the body of the chisel 110 and the recess can be associated with the sleeve 120.

The adjusting mechanism that comprises the OST 122 and IST 132 can be used for moving the leading casing 130 in relation to the sleeve 120, therefore it can be used in order to lead the pointed-edge 114 to a desired starting depth before hamming the top edge 112 of the chisel 110. Thus, controlling the starting point of the emerging of the chisel 110 behind the supporting edge. More information on using the EFCC 100 is disclosed below in conjunction with FIG. 4.

FIG. 2 illustrates a cross-section view of relevant elements of an example embodiment of a motorized-adjustable chisel (MAC) 200 in which a motor 250 is used. MAC 200 is illustrated in a resting stage, before or after activating the chisel. The motor 250 can be an electrical motor or a pneumatic motor, for example. Activating the motor 250 can be done by foot-pedal or by a switch located on the MAC 200 itself. The pedal or the switch are not shown in the figures. An embodiment of the MAC 200 may comprise a chisel-holder (CH) 210, a sleeve 220, a hammer-Housing (HH) 230, an internal hammer (IH) 240 and a set of two or more chisels 219a, and 219b, for example, each may have different pointing edge and different shape or size, in order to fit the different requirements of the different procedures.

The sleeve 220 may have an inner-screw-threaded (IST) 222, and a stopping-ring 224.

The HH 230 may comprise an outer-screw-threaded (OST) 234, a spring-holder ring (SHR) 232 and a motor-carrying mechanism (MCM) 236 that carries the motor 250 and its active arm (AA) 252. The IH 240 may comprise a top section 242, which is associated with the AA 252 during the resting stage and during the activating the motor clockwise (from the reader point of view) and pulling the IH 240 up until a point in which the top section 242 is released from the AA 252. The IH 240 may further comprise a hammering plate (HP) 246, which is adapted to punch on the top section 216 of the CH 210 (TSCH 216).

A mechanical-energy-storage device such as but not limited to a punching spring (PS) 254 can be located around the body of the IH 240 in a compartment that is created between the HP 246 and the SHR 232. The height of the compartment, in the resting stage, depends on the relative position between the stopping-ring 224 of the sleeve 220 and SHR 232 of HH 230. The relative position can be adjusted by rotating and sleeve 220 around the HH 230 and moving along the IST 222 and the OST 234 up or down, decreasing or increasing the height of the compartment (respectively) for adjusting the punching force. In addition the adjusting mechanism of IST 222 and the OST 234 can be used also for setting the emergence of the CH 210 that carries the chisels 219a, or 219b. The hammering force is increased when the height of the compartment is decreased and vice versa. In some embodiments a ruler can be marked on the external walls of the HC 230. Thus, the IST 222 and the OST 234 can be referred as an example of force adjusting mechanism. The ruler can be used for adjusting the stored mechanical energy in the loaded spring which will be converted to the punching force, which will be converted into penetrating force while the chisel penetrates the bone. In the present description and the claims the words punching, harming, striking, may be used interchangeably.

In some embodiments of MAC 200, the sleeve 220 can be replaced with a sleeve that comprises a penetrating section similar to the penetrating section 134 (FIG. 1). Replacing the sleeves can be done by using the OST 234 and the IST 222 and rotating the sleeve 220 around the HH 230 until separating the two units and assembling a sleeve with a penetrating section (not shown in the figures). The sleeve with the penetrating section can have a fix chisel, a changeable chisel, as well as curved section sleeve.

The CH 210 may further comprise a chisel holder 218, an adjusting-screw-threaded 212 and an adjusting-screw ring 214 with inner-screw-threaded. In some embodiments the wall of the sleeve 220 may have an adjustment-window (not shown in the drawings) in the area around the adjusting-screw ring 214 for allowing the movement, up and down, of the ring and enables the doctor to access the ring in order to rotate the adjusting-screw ring 214. In some embodiments two windows can be used, one in each side of the sleeve. The chisel holder 218 can be configured to contain a selected chisel 219a or 219b. The selected chisel is one of the chisels that match the required manipulation of the bone. In some embodiments, the holder 218 can comprise an inner-screw-threaded along the internal walls of the chisel holder 218, while the chisels 219a or 219b can have an outer-screw-threaded, for example. In other embodiments a quick connection mechanism can be used to hold the chisel 219a,b in the CH 210. In such embodiments mounting a selected chisel in the holder 218 can be done by screwing the chisel in the holder 218. The chisel holder 218 engaged with a selected chisel 219a or 219b can be referred as an extended chisel.

The adjusting-screw-threaded 212 and the adjusting-screw ring 214 are used to adjust the scope of the movement of the chisel. The scope of the movement is equal to the distance between the top side of the adjusting-screw ring 214 and the stopping-ring 224 during the resting stage. In some embodiments a ruler can be marked on the external walls of the sleeve 220 close to the adjusting window. The ruler can be used during adjusting the scope of the movement of the chisel in the bone to the required depth. In other embodiments the ruler can be placed on the chisels 219a, or 219b, for example.

In some embodiments of a MAC 200 a following-spring 256 can be located around the body of the CH 210. The following spring 256 is weaker than the PS 254 and is used to follow the movement of the IH 240 when the motor 250 is activated and the AA 252 pull the top section 242 of the IH 240 up to load the PS 254 with an adjusted mechanical energy. The spring constant of the following-spring 256 can be equal to few percentages of the spring constant of the PS 254, 5% to 15% for example. During the movement up of the IH 240, the following-spring 256 push the adjusting ring 214 up until it is blocked by the stopping-ring 224 waiting to be punched by the IH 240.

Alternate embodiments of MAC 200 may not comprise the following spring 256. In such embodiment, the adjusting ring 214 moves up and follow the movement up of the IH 240 by pressing, by the doctor, the chisel against the bone while activating the motor 250.

When the top section 242 is released from the AA 252 the loaded PS 254 can release the stored mechanical energy, which is converted to an elastic force that push the HP 246 of the IH 240 down punching the TSCH 216, which moves toward the bone together with the associate chisel 219a or 219b and manipulates the bone. Along the disclosure the terms move down means move in the direction of the bone and moving up means moving off the bone.

Some example of a MAC 200 may have a moveable SHR 232 that can move up along the left wall of the MCM 236 in order to allow the pulling of the penetrated chisel 219a,b from the manipulated bone. Such embodiments may have a holding SHR-holding mechanism 238 that holds the SHR 232 in order to load the PS 254 with mechanical energy. After releasing the mechanical energy and harming the IH 240, the user can pull the SHR-holding mechanism 238 toward the HH 230 for releasing the SHR 232 and allows the pulling of the chisel manually or by using the motor. More information on operating the MAC 200 is disclosed below in conjunction with FIG. 4.

Referring now to FIG. 3 that illustrates a cross-section view of relevant elements of an example embodiment of a hand-activate-adjustable chisel (HAAC) 300, in which the doctor can load the punching spring 254 by using one or more levers instead of the motor 250 which is disclosed above in conjunction with FIG. 2. HAAC 300 is illustrated in a resting stage, before or after activating the chisel. In the illustrated example of HAAC 300 a lever 352, when it is pulled by a doctor, can be used for compressing the PS 254 in order to load the PS 254 with mechanical energy, for example.

Most of the elements of HAAC 300 are similar to the elements of MAC 200 and having the same numeral as the relevant elements of MAC 200. Those elements are detailed described above in conjunction with FIG. 2 and therefore will not be further described. An example of a lever 352 can comprise three beams 352*a*, 352*b* and 352*c* and a hinge 352*d*. The two beams, 352*a* and 352*b*, are fixed in a predefined angle around the hinge 352*d* by beam 352*c*. In the illustrated example, the beam 352*b* is longer than the beam 352*a*. Pulling the beam 352*b* toward the sleeve 220, by the doctor hand, enforces the IH 240 to move up by beam 352*a* and compressing the PS 254 in order to load it with mechanical energy. The stored mechanical energy is released when the top section 242 is disconnected from the beam 352*a*. The released IH 240 is pushed, by the loaded PS 245, toward the CHTS 216 for punching the CH 220 and the chisel 219*a* or 219*b* that was selected for the current bone manipulation.

Beam 356 is used to connect, via an axis 354, the hinge 352*d* of the lever 352 to the hammer-housing (HH) 230. The axis 354 is used for allowing the movement of the beam 358 freely for associating the beam 352*a* with the top section 242 and during the activation of the lever 352. More information on operating the MAC 200 is disclosed below in conjunction with FIG. 4.

Figure 4:
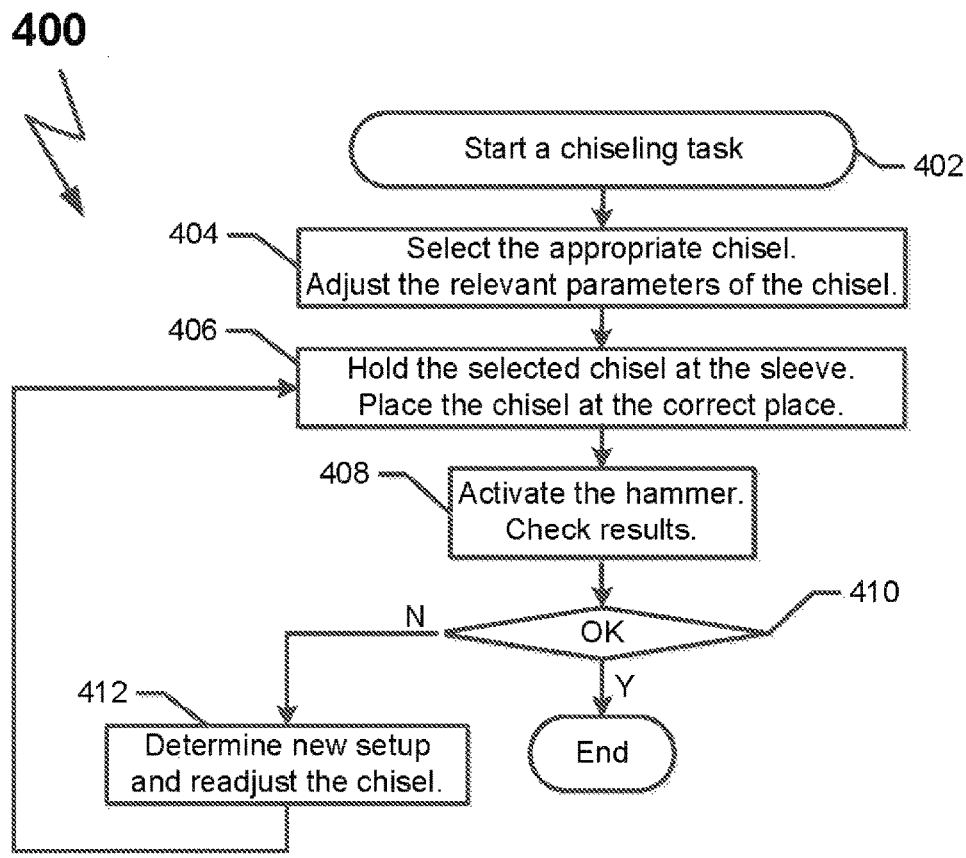
FIG. 4 illustrates a flowchart with relevant actions of an example method of using an embodiment of a configurable chisel.

FIG. 4 illustrates a flowchart with relevant actions of an example method 400 for using an embodiment of a configurable chisel. Method 400 can be implemented by a user, a doctor for example, while manipulating a bone by an embodiment of an adjustable chisel. Upon initiation of the chiseling task 402, the doctor can determine which chisel is needed for the required manipulation and accordingly select 404 the appropriate device. The decision can be based on the scope of movement that is needed, the required force, the shape of the pointed edge (219*a* or 219*b* FIG. 2, for example), a need for a penetrating section 134 (FIG. 1), etc.

Next the appropriate chisel can be adjusted 404 to the required parameters. In cases in which the scope of the movement is important, then an appropriate external-force-configurable chisel (EFCC) 100 can be selected 402. The selection can be based on the length of the recess 116. In some embodiments in which EFCC 100, which has a fine-tuning mechanism that is configured to adjust the starting point of the chisel 110 in relation to the sleeve 120 within the scope of movement which was set by recess 116 and protrusion 124. An example of a fine tuning mechanism can be such as IST 132 and OST 122 (FIG. 1). When such embodiment is used then the starting point of the movement of the chisel in relation to the supporting edge can be fine adjusted 404 by rotating the leading casing 130 around the sleeve 120 and while monitoring the adjusted depth by looking at the ruler 118 for the relevant scope of the movement.

In cases in which a certain force is required, then MAC 200 or HAAC 300 can be selected 402. The scope of the movement can be adjusted 404 by adjusting-screw ring 214. The intensity of the punching force as well as the starting point can be adjusted 404 by rotating the sleeve 220 around the hammer-housing (HH) 230.

After adjusting the required parameters such as the scope of the movement, the punching force, the user can hold 406 the chisel in the protecting sleeve 120, or leading casing 130 or HH 230 or sleeve 220 (FIG. 1 or 2) and place it at the appropriate location attaching to the bone. In case that the appropriate location is in a hole which was already be prepared by drilling, then a chisel with a penetrating section such as penetrating section 134 (FIG. 1) can be selected according to the diameter and the depth of the predrilled hole.

Next the hammer can be activated 408. In cases of using an EFCC 100, an external hammer can be used for punching on the top edge 112 of EFCC 100. The scope of the movement will be limited according to the length of recess 116. The punching force depends on the doctor experience. In case of using an example embodiment of MAC 200 activating the IH 240 can be done by pressing a switch or a pedal for activating the electrical or pneumatic motor 250. In some embodiments two stages can be used. In the first stage the motor is clockwise to the point before the AA 252 releases the top section 242 of the IH 240. The second stage is a trigger to move on and release the top section 242. In such embodiment the doctor can make fine tune to the place and the orientation of the chisel in relation to the bone before releasing the IH 240. In such example process the force and the scope of the movement are controllable and the results of the manipulation can be predicted.

After activating the hammer, the result of the chiseling can be checked 408. If 410 the results are OK, then the process 400 can be terminated. If 410 the results are not OK, then at block 412 the doctor can readjust the force and/or the scope of the movement in order to get the required results and the process 400 return to block 406.

Embodiments of the present disclosure teach how to build and use an adjustable chisel in which the scope of the movement and the punching force can be controlled in order to deliver a predictable and save treatment with minimal medical complications, complications such as broken bone, accidental rupture of the sinus membrane, brain concussion, Vertigo, etc.

The above description is intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled. In the appended claims, the terms "including" and "in which" are used as the plain-English equivalents of the respective terms "comprising" and "wherein".

I claim:

1. An assembly for manipulating a bone in a medical surgery, the assembly comprising:
    an elongated-shaped chisel having a top edge proximate to one end that is configured to interface with an internal hammer, a body, and a pointed edge proximate to the other end, the pointed edge is configured to interface with the bone; and
    an elongated-shaped sleeve that surrounds the body of the elongated-shaped chisel;
    a movement-control mechanism that is configured to control the movement of the elongated-shaped chisel in relationship to the elongated-shaped sleeve, wherein the movement-control mechanism comprises a first section that is associated with the elongated-shaped chisel and a second section that is associated with the elongated-shaped sleeve;
    a hammer-housing that is coupled to the elongated-shaped sleeve on top of the top edge of the elongated-shaped chisel and comprises a punching spring as a mechanical-energy-storage device and an activating mechanism, wherein the activating mechanism comprises a set of beams which are configured to push the hammer away from the chisel upon being manually activated, thereby loading the punching spring with mechanical energy.

2. The assembly of claim 1, wherein the chisel comprises a ruler for indicating the changes in location of the chisel relative to the sleeve.

3. The assembly of claim 1, wherein the first section of the movement-control mechanism is a recess in the chisel and the second section of the movement-control mechanism is a protrusion from the internal wall of the sleeve and penetrates the space of the recess limiting the movement of the chisel in relation to the sleeve according to the recess.

4. The assembly of claim 1, wherein the first section of the movement-control mechanism is a ring that surrounds the chisel and the second section of the movement-control mechanism is a protrusion from the internal wall of the sleeve and limits the scope of the movement of the chisel in relation to the sleeve according to the position of the ring in relation to the protrusion.

5. The assembly of claim 4, wherein the ring has an inner-screw-threaded and the chisel has an outer screw-threaded that are configured to enable the movement of the ring along the body of the chisel for fine adjustment of the scope of the movement of the chisel in relation to the sleeve.

6. The assembly of claim 1, wherein the pointed edge of the chisel can be replaced according to the required manipulation of the bone.

7. The assembly of claim 1, wherein the manipulation is chiseling the bone.

8. The assembly of claim 1, wherein the manipulation is breaking the bone.

9. The assembly of claim 1, wherein the medical surgery is a dental surgery.

10. The assembly of claim 1, wherein the pointed edge of the chisel extents extends out of the sleeve, the assembly further comprising a casing that comprises:
    a. a wide section that surrounds the sleeve and is coupled to the sleeve; and
    b. a penetrating section that surrounds the pointed edge of the chisel without attaching the chisel, wherein the penetrating section has supporting edge that is configured to interface with the bone around the area, which is planned to be manipulated.

11. The assembly of claim 10, wherein the wide section of the casing is coupled to the sleeve by a fine-tuning mechanism that is configured to adjust the location of the casing in relation to the sleeve to set the starting point of the emerging of the chisel in relation to the supporting edge.

12. The assembly of claim 11, wherein the fine-tuning mechanism comprises an inner screw-threaded over the internal walls of the wide section and an outer screw-threaded that when are engaged together are holding the wide section and the sleeve coupled together.

13. The assembly of claim 1, wherein the activating mechanism is further configured to release the loaded mechanical energy by releasing the internal hammer and allowing the punching spring to push the internal hammer toward the top edge of the chisel and punches the top end of the chisel.

14. The assembly of claim 1, wherein the activating mechanism comprises a motor.

15. The assembly of claim 1, wherein the movement-control mechanism comprises:
    c. a ring that surrounds the chisel; and
    d. a protrusion from the internal wall of the sleeve and penetrates the space below the top edge of the chisel and the ring that surrounds the chisel.

16. The assembly of claim 15, wherein the ring that surrounds the chisel has an inner-screw-threaded and the chisel has an outer screw-threaded that are configured to enable the movement of the ring along the body of the chisel for fine adjustment of the scope of the movement of the chisel in relation to the sleeve.

17. The assembly of claim 1, wherein the hammer-housing is coupled to the sleeve by a force adjusting mechanism.

18. The assembly of claim 17, wherein the force adjusting mechanism comprises:
    a. an inner-screw-threaded located at the internal side of the wall of the sleeve; and
    b. an outer screw-threaded that is located on the outer side of the wall of the hammer-housing;
    c. wherein the inner-screw-threaded and the outer screw-threaded are configured to enable relative movement of the sleeve along the hammer-housing for adjusting the compression of the punching spring.

19. The assembly of claim 1, wherein the hammer-housing comprises a mechanism for pulling the chisel from the manipulated bone.

20. A method for manipulating a bone in a medical surgery, the method comprising:
    a. selecting, according to the required manipulation of the bone, an appropriate configurable-chisel that comprises an elongated-shaped chisel and an elongated-shaped sleeve that surrounds the body of the elongated-shaped chisel;
    b. holding the configurable-chisel by the elongated-shaped sleeve;
    c. placing the configurable-chisel at the bone according to the manipulation; and
    d. hammering the elongated-shaped chisel by manually activating a punching spring as a mechanical-energy-storage device, wherein the configurable-chisel comprises a set of beams which are configured to push a hammer away from the configurable-chisel upon being manually activated, thereby loading the punching spring with mechanical energy, which when released causes the hammering.

21. The method of claim 20, wherein selecting the appropriate configurable-chisel is based on the required scope of the movement of the elongated-shaped chisel.

22. The method of claim 20, wherein the configurable-chisel further comprises a casing, then holding the configurable-chisel further comprising: fine tuning the scope of the movement.

23. The method of claim 22, wherein the fine tuning is implemented by rotating the casing around the sleeve.

24. The method of claim 20, wherein hammering the elongated-shaped chisel is implemented by an external hammer.

25. The method of claim 24, wherein holding the configurable-chisel by the elongated-shaped sleeve further comprising adjusting the intensity of the hammering.

26. The method of claim 20, wherein the configurable-chisel further comprises a hammer-housing that is coupled to the sleeve on top of the top edge of the elongated-shaped chisel, then hammering the elongated-shaped chisel is implemented by an internal hammer that is comprised in the hammer-housing.

* * * * *